United States Patent [19]

Ryan

[11] 4,171,315
[45] Oct. 16, 1979

[54] PREPARATION OF CIS-HEXAHYDRODIBENZOPYRANONES

[75] Inventor: Charles W. Ryan, Indianapolis, Ind.

[73] Assignee: Eli Lilly and Company, Indianapolis, Ind.

[21] Appl. No.: 892,350

[22] Filed: Mar. 31, 1978

[51] Int. Cl.$^2$ .......................................... C07D 311/78
[52] U.S. Cl. ................................................ 260/345.3
[58] Field of Search ..................................... 260/345.3

[56] References Cited

U.S. PATENT DOCUMENTS 4,054,581  10/1977  Blanchard et al. ............... 260/345.3

OTHER PUBLICATIONS

March, "Advanced Organic Chemistry: Reaction Mechanism and Structure", McGraw-Hill Book Co., New York, N. Y., 1968, pp. 712–716.
House, "Modern Synthetic Reactions", W. A. Benjamin, Inc., New York, N.Y., 1965, pp. 276–280.
Archer et al., J. Org. Chem., 42, 2277 (1977).

Primary Examiner—Nicky Chan
Attorney, Agent, or Firm—Charles W. Ashbrook; Arthur R. Whale

[57] ABSTRACT

Reaction of 4-(1-hydroxy-1-methylethyl)-3-cyclohexen-1-one with a 5-substituted resorcinol in the presence of boron tribromide, boron trifluoride or stannic chloride provides, depending upon the duration of reaction, either a 2,7-dihydroxy-5-isopropylidene-9-substituted-2,6-methano-3,4,5,6-tetrahydro-2H-1-benzoxocin or a 6a,10a-cis-1-hydroxy-3-substituted-6,6-dimethyl-6,6a,7,8,10,10a-hexahydro-9H-dibenzo[b,d]pyran-9-one.

5 Claims, No Drawings

PREPARATION OF CIS-HEXAHYDRODIBENZOPYRANONES

BACKGROUND OF THE INVENTION

Nabilone is the generic name assigned to 6a,10a-trans-1-hydroxy-3-(1,1-dimethylheptyl)-6,6-dimethyl-6,6a,7,8,10,10a-hexahydro-9H-dibenzo[b,d]pyran-9-one. Nabilone is among a group of trans-hexahydrodibenzopyranones which recently have been found to be particularly useful in the treatment of anxiety, depression and related disorders of the central nervous system; see U.S. Pat. Nos. 3,928,598, 3,944,673 and 3,953,603. In view of the potential clinical usefulness of nabilone and related dibenzopyranones, an extensive effort has been devoted to finding improved and alternative methods for the preparation of such compounds.

The original synthesis of 6a,10a-trans-hexahydrodibenzopyranones suffered from being multistep and of low overall yields, in addition to providing substantial mixtures of 6a,10a-cis and 6a,10a-trans isomers, the separation of which is somewhat difficult; see U.S. Pat. No. 3,507,885. A number of relatively simple one-step syntheses of 6a,10a-cis-hexahydrodibenzopyranones recently have been discovered and are summarized by Archer, et al., *J. Org. Chem.*, 42, 2277 (1977). While a one-step synthesis of 6a,10a-trans-hexahydrodibenzopyranones from relatively simple and inexpensive starting materials has not yet been discovered, a method for conveniently converting the 6a,10a-cis isomers to the corresponding 6a,10a-trans isomers is available; see U.S. Pat. No. 4,054,582.

An object of this invention is to provide an alternative process for preparing 6a,10a-cis-hexahydrodibenzopyranones, which compounds are intermediates in the preparation of the more biologically active 6a,10a-trans isomers, e.g., nabilone.

SUMMARY OF THE INVENTION

This invention relates to the preparation of intermediates useful in the synthesis of 6a,10a-transhexahydrodibenzo[b,d]pyran-9-ones. The invention more particularly provides a process for preparing 6a,10a-cis-hexahydrodibenzo[b,d]pyran-9-ones having the formula

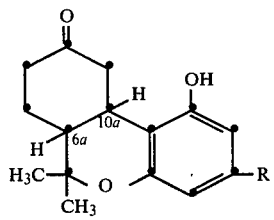

wherein: R is $C_5$–$C_{10}$ alkyl, $C_5$–$C_{10}$ alkenyl, $C_5$–$C_8$ cycloalkyl, or $C_5$–$C_8$ cycloalkenyl; and wherein the hydrogen atoms attached at the 6a and 10a positions are oriented cis to one another; comprising reacting a 5-substituted resorcinol of the formula:

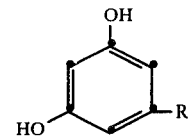

wherein R has the above-defined meaning, with 4-(1-hydroxy-1-methylethyl)-3-cyclohexen-1-one having the formula

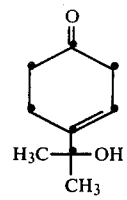

in the presence of boron tribromide, boron trifluoride or stannic chloride in an unreactive organic solvent at a temperature from about −30° C. to about 100° C. for from about 0.5 hours to about 8 hours.

Preferred catalysts for the reaction are boron trifluoride and stannic chloride, and particularly stannic chloride.

A preferred process according to this invention comprises reacting 4-(1-hydroxy-1-methylethyl)-3-cyclohexen-1-one with 5-(1,1-dimethylheptyl)resorcinol in the presence of stannic chloride in dichloromethane to provide 6a,10a-cis-1-hydroxy-3-(1,1-dimethylheptyl)-6,6-dimethyl-6,6a,7,8,10,10a-hexahydro-9H-dibenzo[b,d]pyran-9-one.

DETAILED DESCRIPTION OF THE INVENTION

According to the process of this invention, 4-(1-hydroxy-1-methylethyl)-3-cyclohexen-1-one is condensed with approximately an equimolar quantity of a 5-substituted resorcinol in the presence of a catalyst. In the above formulas, R is defined as $C_5$–$C_{10}$ alkyl, $C_5$–$C_{10}$ alkenyl, $C_5$–$C_8$ cycloalkyl, and $C_5$–$C_8$ cycloalkenyl. Examples of $C_5$–$C_{10}$ alkyl groups include n-pentyl, 1,1-dimethylpentyl, n-hexyl, 1-ethylhexyl, 1,2-dimethylheptyl, 1-ethyl-2-methylhexyl, 1,2,3-trimethylheptyl, n-octyl, 1-methylnonyl, and n-decyl. Similarly, typical $C_5$–$C_{10}$ alkenyl groups include 3-methyl-2-butenyl, 1-pentenyl, 1,2-dimethyl-1-hexenyl, 2-heptenyl, 1-ethyl-2-heptenyl, 1,1-dimethyl-2-octenyl, 3-nonenyl, 1,2-dimethyl-1-heptenyl, and 1methyl-1-nonenyl. R additionally includes $C_5$–$C_8$ cycloalkyl groups such as cyclohexyl, cycloheptyl and cyclooctyl, as well as $C_5$–$C_8$ cycloalkenyl groups such as 1-cyclopentenyl, 1-cyclohexenyl, 2-cycloheptenyl, and 3-cyclooctenyl. Typical 5-substituted resorcinols commonly utilized in the process of this invention thus include 5-(n-pentyl)-resorcinol, 5-(1,2-dimethylheptyl)resorcinol, 5-(1-ethyl-2-methylbutyl)-resorcinol, 5-(n-octyl)resorcinol, 5-(1-hexenyl)resorcinol, 5-(1,2-dimethyl-1-heptenyl)resorcinol, 5-(1-octenyl)resorcinol, 5-cyclopentylresorcinol, 5-cycloheptylresorcinol, 5-(1-cyclohexenyl)resorcinol, 5-(2-cyclooctenyl)resorcinol, and the like.

This invention provides a convenient process for preparing a dl-cis-hexahydro-dibenzo[b,d]pyran-9-one. As used herein, the term "cis" refers to the orientation relative to one another of the hydrogen atoms attached at the 6a and 10a positions of a dibenzopyranone compound represented by the above formula. Accordingly, compounds which are designated as being "cis" are those dibenzopyranones of the above formula wherein the hydrogen atoms attached at the 6a and the 10a positions are oriented on the same side of the plane of the molecule. It will be recognized that at least two isomers are included by the "cis" designation. In particular, both the 6a hydrogen atom and the 10a hydrogen atom can be oriented above the plane of the molecule, in which case their absolute configuration is designated as 6a$\beta$ and 10a$\beta$. Alternatively, both the 6a hydrogen atom and the 10a hydrogen atom can be oriented below the plane of the molecule, in which case they are designated as 6a$\alpha$ and 10a$\alpha$.

The absolute configuration of the 6a-hydrogen atom and the 10a-hydrogen atom will not hereinafter be designated; rather, it is to be understood that the designation "cis" includes the separate mirror image isomers of the compounds having the above general formula, as well as the dl mixture of such mirror image isomers. For example, a 6a,10a-cis compound prepared by the process of this invention will be understood to include the 6a$\alpha$,10a$\alpha$-isomer, as well as the 6a$\beta$,10a$\beta$ isomer, or a mixture of said mirror images. Such mixture of mirror image isomers will be designated in the normal manner as a dl-mixture, and is the usual product of the present process.

The process provided by this invention is carried out by mixing approximately equimolar quantities of a 5-substituted resorcinol, as hereinabove defined, and 4-(1-hydroxy-1-methylethyl)-3-cyclohexen-1-one, in an unreactive organic solvent and in the presence of a catalyst selected from boron tribromide, boron trifluoride and stannic chloride. Unreactive organic solvents commonly used in the process include halogenated hydrocarbons such as dichloromethane, chloroform, 1,2-dibromoethane, 1-bromo-2-chloroethane, 1,1-dibromoethane, 2-chloropropane, 1-iodopropane, chlorobenzene, bromobenzene, and 1,2-dichlorobenzene; aromatic solvents such as benzene, toluene, and xylene; and ethers such as diethyl ether, methyl ethyl ether, dimethyl ether, and diisopropyl ether. Preferred unreactive organic solvents include the halogenated hydrocarbons and the aromatic solvents. A preferred catalyst for the reaction is stannic chloride. When boron trifluoride is utilized as condensation catalyst, it generally is utilized as the commercially available diethyl etherate complex. The quantity of catalyst generally incorporated in the process ranges from about an equimolar quantity, relative to the resorcinol and cyclohexenone reactants, to an excess of about 0.1 to about a 5 molar excess. The process of this invention can be carried out at a temperature in the range of from about −30° C. to about 100° C., and is most conveniently carried out at a temperature in the range of from about −25° C. to about 40° C., especially from about −25° C. to about +25° C. As an example, a resorcinol such as 5-(n-pentyl)-resorcinol is mixed with about an equimolar quantity or slight excess (0.1 to 0.5 molar excess) of 4-(1-hydroxy-1-methylethyl)-3-cyclohexen-1-one in a solvent such as benzene. A catalyst such as boron trifluoride diethyl etherate is added in the amount of about a 0.1 to about a 5 molar excess. The reaction is conducted at a temperature in the range of about −25° C. to about 50° C., and is substantially complete within about 0.5 to about 8 hours to provide the 3-n-pentyl hexahydrodibenzopyranone. Longer reaction times appear not to be detrimental to the process and can be utilized if desired.

Upon completion of the reaction of a 5-substituted resorcinol and the aforementioned cyclohexenone derivative according to the above-recited process conditions, the product, a dl-cis-1-hydroxy-3-substituted-6,6-dimethyl-6,6a,7,8,10,10a-hexahydro-9H-dibenzo[b,d]-pyran-9-one, can be isolated if desired by simply washing the reaction mixture with an aqueous acid or an aqueous base, or both successively, followed by washing the reaction mixture with water. The organic solvent layer is then separated and the solvent is removed therefrom, for example by evaporation. Aqueous acids commonly used to wash the reaction mixture include dilute aqueous hydrochloric acid and dilute aqueous sulfuric acid, for instance 0.5 to about 6 normal aqueous acids. Commonly used aqueous bases include 0.1 to 1.0 N sodium hydroxide, as well as saturated sodium bicarbonate solutions. Once the product of the reaction is isolated by removal of the reaction solvent, no further purification generally is required, although the product can be recrystallized from solvents such as n-hexane and cyclohexane if desired. The product produced according to the process of this invention is substantially exclusively the dl-cis-isomer of a 1-hydroxy-3-substituted-6,6-dimethyl-6,6a,7,8,10,10a-hexahydro-9H-dibenzo[b,d]pyran-9-one, although small quantities on the order of about 5 to about 15 percent by weight of the corresponding dl-trans isomer generally can be detected. Purification of such mixture to remove the trans isomers which are present is unnecessary since the major product, namely the dl-cis-hexahydrodibenzopyranone, is generally transformed to the pure dl-trans isomer by treatment with an aluminum halide, as is described in more detail hereinbelow. Such conversion can be carried out in situ if so desired, thereby obviating the need for isolation of the cis intermediate.

It should be noted that the cis-hexahydrodibenzo[b,d]pyranones prepared according to this invention are prepared when the reaction between a resorcinol and the cyclohexenone is allowed to continue for from about 0.5 to about 8 hours. When the reaction is stopped as soon as the catalyst is added to the reaction mixture, a benzoxocin is the product. For example, reaction of 4-(1-hydroxy-1-methylethyl)-3-cyclohexen-1-one with a resorcinol such as 5-(1,2-dimethylheptyl)resorcinol in a solvent such as benzene and in the presence of stannic chloride for about two minutes provides a benzoxocin, namely 2,7-dihydroxy-5-isopropylidene-9-(1,2-dimethylheptyl)-2,6-methano-2H-1-benzoxocin. The reaction is quenched by simply diluting the reaction mixture with water or ice, and the product can be isolated by simple extraction with a water immiscible solvent such as benzene. The benzoxocin derivatives which can thus be prepared are disclosed in U.S. Pat. No. 4,054,583. Such patent also describes the conversion of such benzoxocin derivatives to 6a,10a-trans-hexahydrodibenzopyranones by reaction with an aluminum halide. The benzoxocin derivatives also are converted to the corresponding 6a,10a-cis-hexahydrodibenzopyranone by reaction with catalysts such as stannic chloride, and it should be apparent that such benzoxocin derivatives are initially formed in the process of this invention. If desired, such intermediates can be isolated and purified for later conversion to either cis or trans-hexahydrodibenzopyranones, but it is preferred to simply prepare the cis-hexahydrodibenzopyranones according to this invention, and then convert such cis isomers to the corresponding trans isomers as described in U.S. Pat. No. 4,054,582.

Reaction of a dl-cis-hexahydrodibenzopyranone prepared according to this invention with an aluminum halide such as aluminum bromide or aluminum chloride in a halogenated hydrocarbon solvent such as dichloromethane effects total epimerization to afford exclusively the corresponding dl-trans-hexahydrodibenzopyranone. As an example, dl-cis-1-hydroxy-3-(1,1-dimethylheptyl)-6,6-dimethyl-6,6a,7,8,10,10a-hexahydro-9H-dibenzo[b,d]pyran-9-one, which is prepared in about 80 to about 85 percent yield in accordance with the process of this invention, can be reacted with about a 3 to 4 molar excess of aluminum chloride in dichloromethane at a temperature of about 25° C. to provide exclusively dl-trans-1-hydroxy-3-(1,1-dimethylheptyl)-6,6-dimethyl-6,6a,7,8,10,10a-hexahydro-9H-dibenzo[b,d]pyran-9-one, i.e., nabilone. As noted hereinbefore, such trans-hexahydrodibenzopyranones are particularly useful in the treatment of anxiety and depression.

The following detailed examples further illustrate the process of this invention.

EXAMPLE 1

4-(1-Hydroxy-1-methylethyl)-3-cyclohexen-1-one

A solution of 10.0 g. of 4-(1-hydroxy-1-methylethyl)-1-methoxy-1,4-cyclohexadiene in 80 ml. of 2 percent aqueous acetic acid solution was stirred for two hours at 25° C. The acidic solution then was extracted with dichloromethane, and the organic extracts were combined, washed with water and dried. Removal of the solvent by evaporation under reduced pressure provided 7.3 g. of 4-(1-hydroxy-1-methylethyl)-3-cyclohexen-1-one. NMR (CDCl$_3$): §5.8 (t, 1H); §1.9 (s, 1H, OH), §1.33 (s, 6H); m/e: 154 (M+).

EXAMPLE 2

2,7-Dihydroxy-5-isopropylidene-9-(1,1-dimethylheptyl)-2,6-methane-3,4,5,6-tetrahydro-2H-1-benzoxocin A solution of 2.36 g. of 5-(1,1-dimethylheptyl)resorcinol in 50 ml. of dichloromethane containing 1.85 g. of 4-(1-hydroxy-1-methylethyl)-3-cyclohexen-1-one was stirred and cooled to −22° C. in a dry ice-ethanol bath. To the cold stirred solution was added dropwise over 2 minutes 2.5 ml. of stannic chloride. Immediately following the addition, the reaction mixture was poured into 50 g. of ice, and the mixture then was allowed to warm to room temperature. The organic layer was separated, washed with 50 ml. of 1 N sodium hydroxide and with water, and then dried. Evaporation of the solvent afforded a solid residue which was washed with 25 ml. of warm hexane and then dried to provide 3.06 g. (82%) of 2,7-dihydroxy-5-isopropylidene-9-(1,1-dimethylheptyl)-2,6-methane-3,4,5,6-tetrahydro-2H-1-benzoxocin. M.P. 158°–159° C.

EXAMPLE 3 dl-cis-1-Hydroxy-3-(1,1-dimethylheptyl)-6,6-dimethyl-6,6a,7,8,10,10a-hexahydro-9H-dibenzo[b,d]pyran-9-one A solution of 2.36 g. of 5-(1,1-dimethylheptyl)resorcinol in 50 ml. of dichloromethane containing 1.85 g. of 4-(1-hydroxy-1-methylethyl)-3-cyclohexen-1-one was stirred and cooled to −22° C. in a dry ice-ethanol bath. To the cold stirred solution was added dropwise over 2 minutes 2.5 ml. of stannic chloride. Following complete addition of the stannic chloride, the reaction mixture was stirred for 6½ hours at −10° C., after which time the reaction mixture was added to 50 g. of ice and the mixture was permitted to warm to room temperature. The organic layer next was separated, washed with 50 ml. of 1 N sodium hydroxide and with water, and then dried. Removal of the solvent by evaporation under reduced pressure provided 3.1 g. (83%) of dl-cis-1-hydroxy-3-(1,1-dimethylheptyl)-6,6-dimethyl-6,6a,7,8,10,10a-hexahydro-9H-dibenzo[b,d]pyran-9-one. M.P. 154°–162° C. Thin layer chromatographic analysis indicated the product contained about 10% of the 6a,10a-trans isomer.

I claim:

1. A process for preparing a 6a,10a-cis-hexahydrodibenzopyranone of the formula

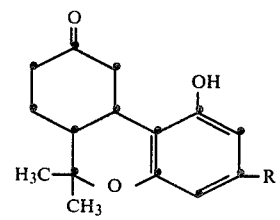

wherein:
R is C$_5$–C$_{10}$ alkyl, C$_5$–C$_{10}$ alkenyl, C$_5$–C$_8$ cycloalkyl or C$_5$–C$_8$ cycloalkenyl, comprising reacting 4-(1-hydroxy-1-methylethyl)-3-cyclohexen-1-one with a 5-substituted resorcinol of the formula

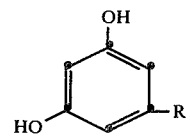

wherein R has the above-defined meaning, in the presence of a catalyst selected from boron tribromide, boron trifluoride and stannic chloride, in an unreactive organic solvent at a temperature from about −30° C. to about 100° C. for from about 0.5 to about 8 hours.

2. The process of claim 1 wherein the catalyst is stannic chloride.

3. The process of claim 2 wherein the unreactive organic solvent is a halogenated hydrocarbon.

4. The process of claim 3 wherein the temperature is from about −25° C. to about +25° C.

5. The process of claim 4, said process comprising reacting 4-(1-hydroxy-1-methylethyl)-3-cyclohexen-1-one with 5-(1,1-dimethylheptyl)resorcinol in dichloromethane to provide dl-6a,10a-trans-1-hydroxy-3-(1,1-dimethylheptyl)-6,6-dimethyl-6,6a,7,8,10,10a-hexahydro-9H-dibenzo[b,d]pyran-9-one.

* * * * *